May 11, 1965 A. M. SHAMMARELLO Plant Pat. 2,508
AZALEA PLANT
Filed Jan. 28, 1964
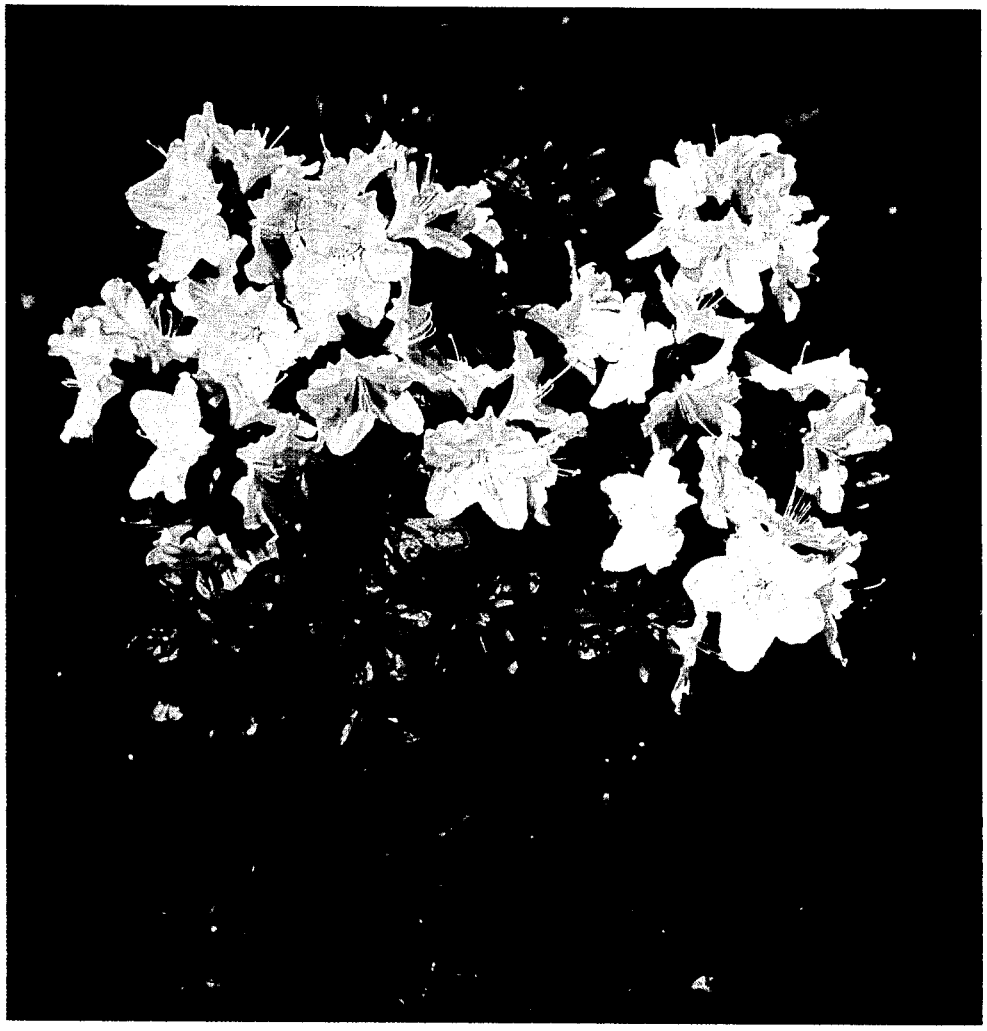

United States Patent Office

Plant Pat. 2,508
Patented May 11, 1965

2,508
AZALEA PLANT

Anthony M. Shammarello, 4590 Monticello Blvd., Cleveland, Ohio

Filed Jan. 28, 1964, Ser. No. 340,839
1 Claim. (Cl. Plt.—55)

The present invention relates to a new and distinct variety of azalea plant of the Kurume type, and is the result of a definite breeding program.

The principal object of this breeding program was to produce a new hardy dwarf white azalea similar in character of growth to the Hino-Crimson parent, with larger flowers than Hino-Crimson. Such a plant to the best of my knowledge is not heretofore known in northern Ohio.

The foregoing objective has been obtained in my new variety, which is characterized by a hardier plant, hardier flower buds, larger flowers than the Kurume parent and the retention of foliage throughout the winter season, together with the bushy character of growth of the Kurume parent.

*Seed parent.*—An unnamed seedling derived from crossing Hino-Crimson × Poukhanense.

*Pollen parent.*—Azalea Desiree—Plant Patent No. 2,068, granted July 4, 1961, to Anthony M. Shammarello, the applicant herein.

All other parents are not patented except Desiree No. 2,068.

My new variety has been found to retain its distinctive characteristics through successive asexual reproduction by means of cuttings in the vicinity of South Euclid, Ohio.

The hardiness of the plant and flower buds of my new variety is indicated by the fact that they were not adversely affected by a temperature of −15° F. during the winter of 1961–1962 in the vicinity of South Euclid, Ohio.

The flowers of my new variety are almost twice the size of the Kurume parent.

The accompanying drawing, forming a part hereof, shows a typical plant of my new variety of azalea, the color of the latter being as nearly true as it is reasonably possible to make the same in a color illustration of this character.

The following is a detailed description of my new variety of azalea plant, color references being to Munsell Neutral Value Scale published by Munsell Color Company.

Type: Hardy-evergreen.
Parentage: Seedling.
*Seed parent.*—An unnamed azalea (azalea Hino-Crimson × Poukhanense).
*Pollen parent.*—Azalea Desiree Plant Patent 2,068.

*Plant*

Form of plant: Bushy-compact.
Growth habit: Medium; low branched; from a cutting attaining a height of about eighteen inches and a width of about three feet in ten years.
Blooming season: About May 10. (Color reference below to Nickerson Color Fan as published by Munsell Color Company.)
Young shoots: Stems—color 2.5GY 6/8 strong yellow green.
Mature shoots: Stems—color 10YR 4/4 moderate yellowish brown.
Foliage:
*Color of young leaves (obverse).*—7.5GY 6/8 strong yellow green.
*Color of mature leaves (obverse).*—7.5GY 5/7 moderate yellow green.
*Color of leaves (reverse).*—7.5GY 4/4 moderate olive green.
*Pubescence of leaves.*—Short white hairs on about 25 percent of underside area.
*Arrangement of leaves*—In a spiral.
*Texture of leaves.*—Firm.
*Form of leaves.*—Ovate.
*Size of leaves.*—1¼″ to 1½″ long.
*Size of leaves.*—½″ to ⅜″ wide.

*Flower*

Type: Single.
Borne: Usually three in a cluster.
Quantity: Abundant.
Form: Five petals, margins of lobes slightly frilled.
Size: Petal spread 1¾″ to 2″ wide.
Texture of petal: Firm.
Blotch: None.
Color: White N9.5, 90% R. (Color reference to Munsell Neutral Value Scale.)
Fragrance: None.
Stamens: 9 to 10; color—white.

I claim:

A new and distinct variety of azalea plant of the hardy evergreen type, substantially as herein shown and described, characterized particularly as to novelty by the hardiness of the plant and buds at low temperatures greater than the parent Hino-Crimson, by flowers larger than the parent Hino-Crimson, and retaining the bushy dwarf character of Hino-Crimson.

No references cited.

T. GRAHAM CRAVER, *Primary Examiner.*